US00PP33343P2

(12) United States Plant Patent
Clark

(10) Patent No.: US PP33,343 P2
(45) Date of Patent: Aug. 10, 2021

(54) COLEUS PLANT NAMED 'UF17-128-7'

(50) Latin Name: *Plectranthus scutellarioides*
Varietal Denomination: UF17-128-7

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 16/974,432

(22) Filed: Jan. 30, 2021

(51) Int. Cl.
*A01H 5/12* (2018.01)

(52) U.S. Cl.
USPC ..... Plt./469

(58) Field of Classification Search
USPC ..... Plt./469
CPC ..... A01H 6/00; A01H 5/12
See application file for complete search history.

(56) References Cited

U.S. PATENT DOCUMENTS

PP32,778 P3 1/2021 Clark

*Primary Examiner* — Keith O. Robinson
(74) *Attorney, Agent, or Firm* — Katherine Koenig; Koenig IP Works, PLLC

(57) ABSTRACT

A new and distinct cultivar of *Plectranthus scutellarioides* (*Coleus*) named 'UF17-128-7', selected for having novel color patterning with excellent color stability and field performance. It is a vigorous well-branched plant with a spreading form, with leaves having striking magenta tones in their centers, and well defined maroon netted venation. Because of this color combination, 'UF17-128-7' is novel, and has no direct comparison in the industry. It has consistent vigor, making it a plant suitable for efficient production in both small and large containers. It is a non-flowering genotype and performs well in both sun and shade, maintaining good consistent color and habit late into the summer garden season.

3 Drawing Sheets

Genus and species: *Plectranthus scutellarioides*.

Cultivar denomination: The present disclosure relates to *Coleus* cultivar 'UF17-128-7'.

CROSS-REFERENCE TO RELATED APPLCIATIONS

N/A.

ACKNOWLEDGEMENT OF FEDERAL RESEARCH SUPPORT

N/A.

BACKGROUND OF THE NEW CULTIVAR

*Coleus* (previously *Solenostemon scutellarioides*, now *Plectranthus scutellarioides*) plants are used as annual bedding plants for the landscape and mixed containers in summer gardens. *Coleus* plants are popular for commercial growers and landscapers because they are easy to propagate and provide fast and reliable attractive foliage color that performs well at all points in the perishable garden plant supply chain. *Coleus* plants are also popular with home gardeners because they are easy to grow in both full sun and partial shade conditions, and require less maintenance than many other annual garden plants. From the breeder perspective, there is much genotypic variability in *Coleus* because it is a tetraploid with active transposons and there are a number of different visible phenotypes including foliage color, leaf shape and size, plant height, time to flowering, and growth habit.

The *Coleus* breeding program at the University of Florida (UF) in Gainesville, Fla., was initiated in 2003 with an emphasis on developing new clonally propagated cultivars that are profitable for producers and perform well in consumer gardens with little or no care. Using recurrent mass selection and maintaining a large pool of germplasm our program has released over 85 new cultivars into the industry since 2007. The *Coleus* breeding program has focused on screening for new cultivars with novel leaf colors and shapes, increased vigor and branching, and late flowering, by conducting greenhouse and field trials under demanding environmental conditions. Greenhouse trials under "lush" conditions that push the plants to grow as fast as possible with high amounts of light, high fertility and high temperatures are used because these conditions allow for rapid discernment of growth habits and vigor characteristics, and also facilitate observation of plant phenotypes under conditions where greenhouse pathogen and insect pressure is highest. A first group of field trials in Citra, Fla., are planted in full sun in sand beds with plastic mulch in May-June each year with drip irrigation, minimal added fertilizer, and no chemical control for insects or pathogens. A second group of field trials in Citra, Fla., are planted in 30% shade in sand beds in May-June each year with drip irrigation and a minimal amount of slow-release fertilizer added at planting. These "lean" growing conditions are used in the field trials to screen for plants that grow vigorously and consistently for minimalist gardeners. *Coleus* produces a better seed crop under "lean" conditions than "lush" conditions, which is useful for making open-pollinated seeds. Since data is collected on a large number of genotypes (~600-800 per year), each trial only contains 1-3 plants per genotype. If a genotype performs poorly in any trial it is automatically discarded from the program, leaving ~200-250 genotypes in the program as elite stock at the end of each year.

Desirable characteristics that continue to be in demand a decade after first commercial introductions are: (1) foliage color stability in sun and shade; (2) consistent well-branched plant habit; and (3) late flowering. Improved plants with interesting foliage colors in both full sun and shade conditions allow for more versatile garden use and more color choices for gardeners. Superior well-branched plant habit is important throughout the production chain from the propagator/grower to the consumer, which allows for production of a large number of vegetative propagules and translates into more manageable plants for producers during culture and shipping to retail outlets. Once planted in the garden, these well-branched plants require less management over a long season of growth. Late flowering is a desirable characteristic because early flowering triggers senescence of the lower leaves and decreases foliage quality of *Coleus*. Floral induction often slows vegetative growth, and increases landscape maintenance with manual dead-heading and plant replacement, which is vital to landscape contractors. Late or 'no flowering' genotypes with good branching and stable foliage color that have been developed at UF have performed well in commercial markets, and continue to attract interest from US, European, and Asian gardeners. The UF genotype disclosed herein was selected because it has many of these desirable traits.

SUMMARY OF THE INVENTION

The invention relates to a new and distinct cultivar of *Coleus* plant named 'UF17-128-7'. The new cultivar 'UF17-128-7' originated from an open pollination conducted in May-November 2016 in Gainesville, Fla., between the female *Coleus* plant 'UF15-96-16' (unpatented) and an unknown male *Coleus* plant. A single seedling was chosen in May 2016 for further asexual propagation in Gainesville, Fla. FIG. 1 shows the pedigree of 'UF17-128-7'.

The new cultivar 'UF17-128-7' has been reproduced asexually for over eighteen (18) months through vegetative cuttings and has been found to retain its distinctive characteristics through successive asexual propagations. 'UF17-128-7' was first propagated asexually by meristem tip cuttings in May 2016 in Gainesville, Fla., and has remained true-to-type since that time.

The new *Coleus* cultivar 'UF17-128-7' has not been observed under all possible environmental conditions. The phenotype of the new cultivar may vary with variations in environment and cultural practices such as temperature, light intensity, fertilization, irrigation, and application of plant growth regulators without any change in genotype.

Plant Breeder's Rights for 'UF17-128-7' have not been applied for. The new *Coleus* cultivar 'UF17-128-7' has not been made publicly available more than one year prior to the filing date of this application.

The new cultivar 'UF17-128-7' was selected along with its sibling 'UF17-128-17' (U.S. Plant Pat. No. 32,778) because they were the first plants from our program with leaves colored cream, pink, maroon, and chartreuse colored and with enough vigor to withstand the harsh selection conditions our plants are subjected to in full sun trials in Gainesville, Fla. Normally this color combination fades in full sun with the consistent loss of pink color and a browning of the maroon sections of the foliage. The new cultivar 'UF17-128-7' is exceptional because it maintains all three distinct colors in well-defined zones in shade or sun.

The following are the most outstanding and distinguishing characteristics of the new cultivar 'UF17-128-7' when grown under normal horticultural practices in Gainesville, Fla.:

1. a combination of vigorous, compact, upright growth habit, excellent heat tolerance, and leaves consistently colored pink, maroon, and lime green that are significantly different than other *Coleus* plants;
2. superior stability in foliage color in both sun and shade conditions, maintaining stable color in all conditions;
3. a vigorous but compact upright growth habit with excellent lateral branching when grown as a stock plant, thus providing ample vegetative propagules for producers; and
4. 'UF17-128-7' has been observed to have long-season performance in landscape trials in Gainesville, Fla.

Plants of the new *Coleus* cultivar 'UF17-128-7' differ from plants of the female parent, 'UF15-96-16', in the following characteristics:

1. 'UF17-128-7' has large leaves that are contrasting cream, pink, maroon, and lime green and pointed at the apex, while 'UF15-96-16' has smaller leaves colored pink, maroon and lime green that are rounded at the apex; and
2. 'UF17-128-7' has a robust, well-branched mounded habit, whereas 'UF15-96-16' is much less vigorous, and much more upright in habit with less lateral branching.

DESCRIPTION OF THE FIGURES

The accompanying photographs (as shown in FIGS. 1-3) illustrate the overall appearance of the new *Coleus* cultivar 'UF17-128-7'. The colors shown in these photographs are as true as can be reasonably obtained by conventional photographic procedures. Colors shown in the photographs may differ slightly from the color values cited in the detailed botanical description, which accurately describes the colors of the new *Coleus* cultivar.

FIG. 2 shows the growth habit, form, and foliage of 'UF17-128-7'; and

FIG. 3 shows a close-up of the foliage of 'UF17-128-7'.

DETAILED BOTANICAL DESCRIPTION OF THE CULTIVAR

Figure 1:
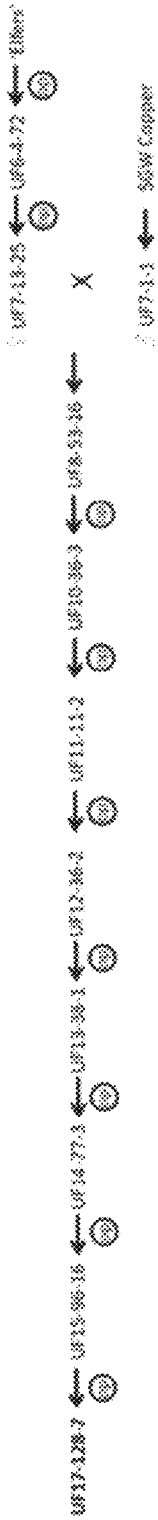
FIG. 1 shows the pedigree of 'UF17-128-7'.
Figure 2:
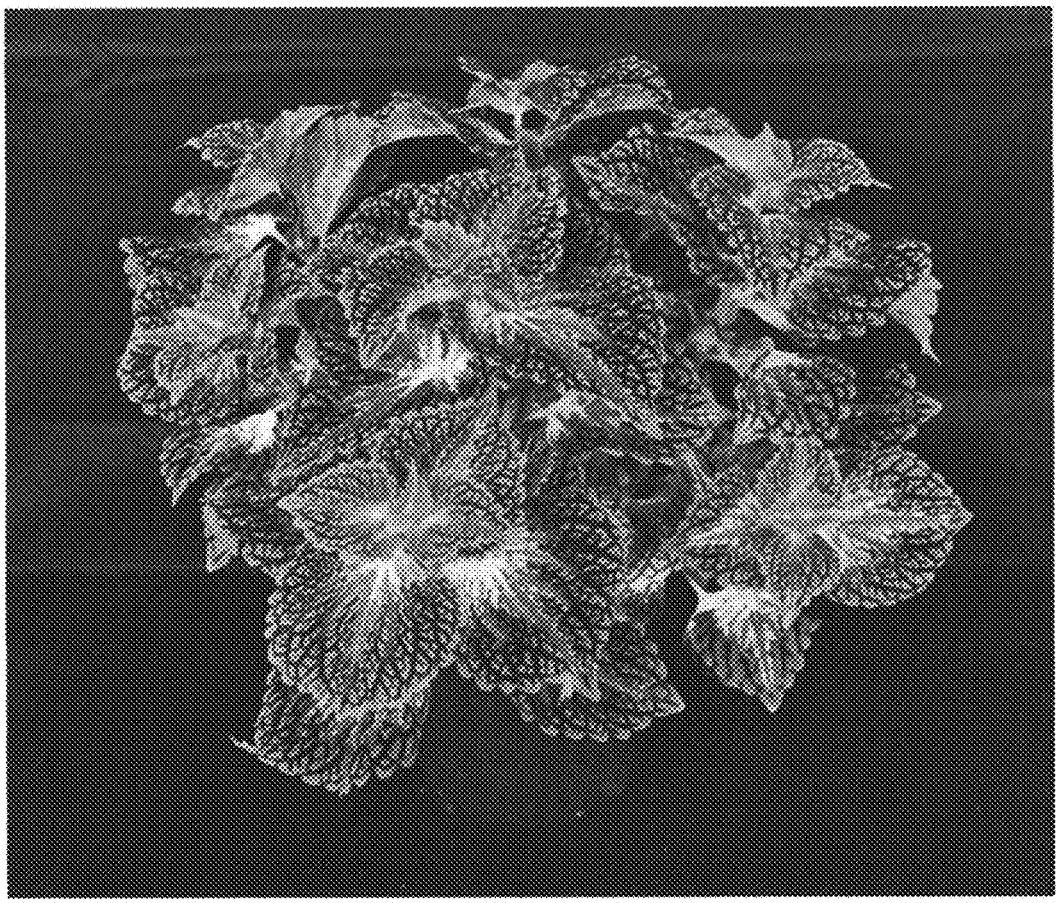
FIGS. 2 and 3 were taken from plants grown nine (9) weeks from unrooted cuttings in June-August 2020 in a glass-covered greenhouse in Gainesville, Fla.
Figure 3:
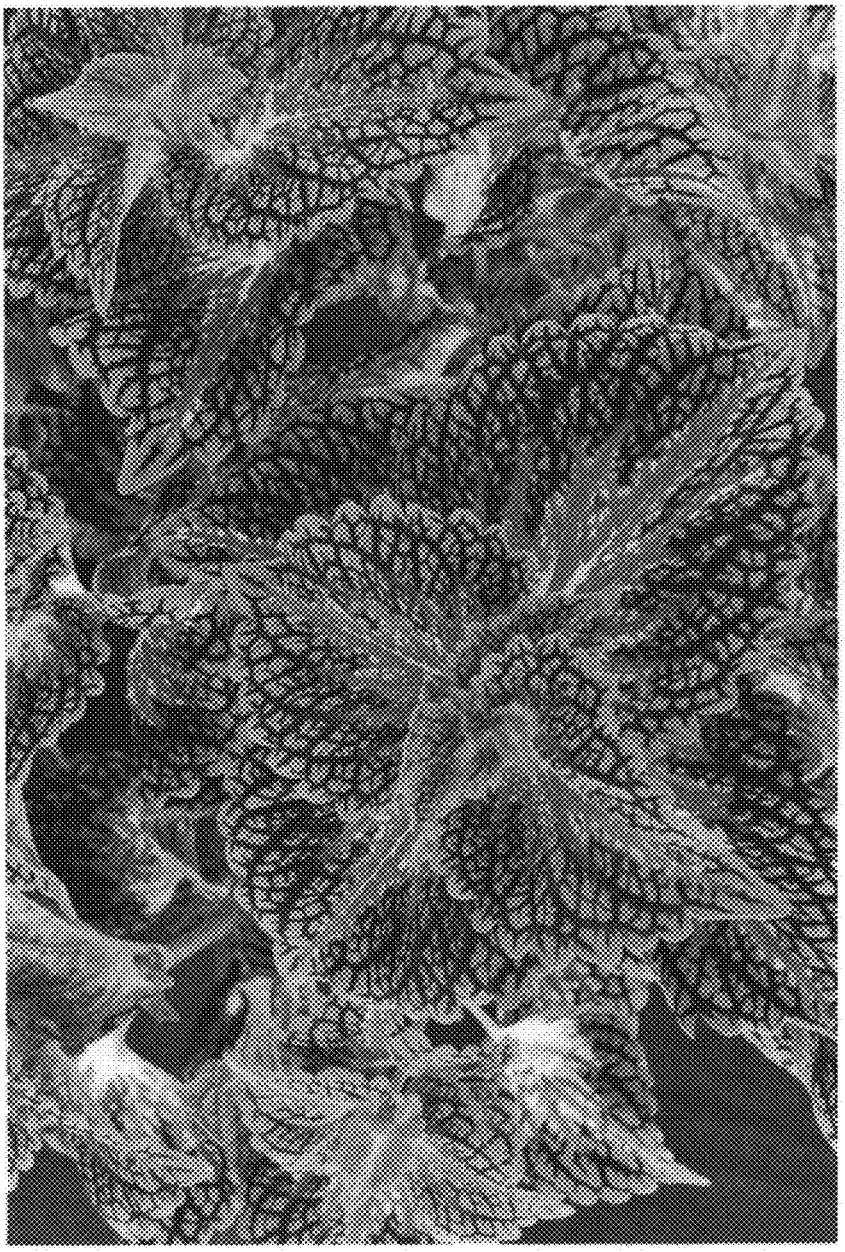

The following detailed description sets forth the distinctive characteristics of the new *Coleus* cultivar 'UF17-128-7'. Color references are to The Royal Horticultural Society of London (R.H.S.) Colour Chart, 2007 (5th Edition).

Description of Growing Conditions

The detailed description was obtained using nine-week-old plants grown from unrooted cuttings in June-August 2020 in a glass-covered greenhouse in Gainesville, Fla. The plants were propagated in mist for ten (10) days after cuttings were stuck, then grown in one-gallon pots for approximately seven and a half additional weeks.

Botanical Description

Botanical classification:

*Family*.—Lamiaceae.

*Botanical name*.—*Plectranthus scutellarioides*.

*Common name*.—*Coleus*.

*Cultivar*.—'UF17-128-7'.

Parentage:

*Female or seed parent*.—'UF15-96-16'.

*Male or pollen parent*.—Unknown.

Propagation:

*Type*.—Vegetative meristems having at least one (1) node.

*Time to initiate roots*.—3-4 days.

*Time to produce a rooted cutting*.—7-10 days.

Root description:

*Root description*.—Callus forms in 2-3 days, roots initiate in 3-4 days and become a highly branched cutting in 7-10 days.

*Rooting habit*.—Fibrous.

Plant description:

*Plant form*.—Spreading.

*Growth habit*.—Upright.

*Plant height* (*from top of soil*).—25-28 cm.

*Plant width* (*horizontal plant diameter*).—40-45 cm.

*Branches*.—Quantity per plant: 7. Branch color: RHS 141C (medium green). Texture: Smooth. Pubescence: Not present. Stem description: Square-shaped stem, 0.8 cm in diameter at the soil line. Branch diameter: 0.6-0.7 cm at the base of a 25-cm long branch. Branch length: 23-27 cm. Internode length: 3-4 cm. Anthocyanin: Not present.

Foliage description:

*Quantity of leaves per branch*.—14-16.

*Arrangement*.—Opposite.

*Fragrance*.—Not fragrant.

*Length*.—10-12 cm.

*Width*.—10-11 cm.

*Shape*.—Ovate. Apex: Broadly acute. Base: Attenuate.

*Margin*.—Crenate.

*Leaf texture* (*both surfaces*).—Smooth.

*Pubescence color* (*both surfaces*).—Not present.

*Color, immature leaf*.—Upper surface, base: RHS 150B (medium yellow green). Upper surface, center: RHS 59C (dark purple). Upper surface, mid-center/veins: RHS 202A (black). Upper surface, margin: RHS 140A (medium green). Lower surface, base: RHS 150B (medium yellow green). Lower surface, center: RHS 59A (dark purple red). Lower surface, mid-center/veins: RHS 187A (dark brown). Lower surface, margin: RHS 145C (light green).

*Color, mature leaf*.—Upper surface, base: RHS 150D (light yellow). Upper surface, center: RHS 58A (dark purple). Upper surface, mid-center/veins: RHS N77A (dark brown). Upper surface, margin: RHS 144A (medium green). Lower surface, base: RHS 3D (light yellow). Lower surface, center: RHS 58B (medium purple red). Lower surface, mid-center/veins: RHS N77A (dark brown). Lower surface, margin: RHS 143B (medium green).

*Venation color*.—Upper surface, base: RHS 145C (light green). Upper surface, edge: RHS 59A (dark purple red). Lower surface, center: RHS 145C (light green).

*Venation pattern*.—Upper surface: Reticulate. Lower surface: Reticulate.

*Petiole length*.—2.0-2.5 cm.

*Petiole diameter*.—0.2-0.3 cm.

*Petiole color*.—RHS 142B.

*Petiole texture*.—Smooth, no pubescence.

Flowers and seeds: Flowers and seeds have not been observed to date during formal trials in Gainesville, Fla.

Fruit/seed set: Fruit and seeds have not been observed to date during formal trials in Gainesville, Fla.

Disease and insect resistance: Disease and insect resistance is typical of the species, thus no claims are made of any superior disease or insect resistance with this cultivar. The most common insect pests observed on this plant in Gainesville, Fla. have been long-tailed or citrus mealybugs (*Pseudococcus* sp.), which occur on older stock plant material held in the greenhouse for over 3-4 months. *Impatiens* Necrotic Spot Virus (Bunyaviridae) has also been observed in plants confined in greenhouses with mixed crops (peppers) infected with Western flower thrips (*Frankliniella occidentalis*). The most common pathogen of this species in the U.S. is downy mildew (*Pernonspora lamii*). This pathogen has been observed in stock materials grown closely together in cooler growing seasons.

What is claimed is:

1. A new and distinct *Plectranthus scutellarioides* plant named 'UF17-128-7' as shown and described herein.

* * * * *